US00PP32803P2

(12) United States Plant Patent
Murray

(10) Patent No.: US PP32,803 P2
(45) Date of Patent: Feb. 9, 2021

(54) ***LOMANDRA* PLANT NAMED 'OLIVE GREEN'**

(50) Latin Name: *Lomandra confertifolia*
Varietal Denomination: Olive Green

(71) Applicant: Ausplanz Investments Pty. Ltd., Wonga Park (AU)

(72) Inventor: Joseph Murray, San Remo (AU)

(73) Assignee: AUSPLANZ INVESTMENTS PTY. LTD., Wonga Park (AU)

( * ) Notice: Subject to any disclaimer, the term of this patent is extended or adjusted under 35 U.S.C. 154(b) by 0 days.

(21) Appl. No.: 16/873,179

(22) Filed: Feb. 20, 2020

(51) Int. Cl.
*A01H 5/02* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/02; A01H 6/00
See application file for complete search history.

*Primary Examiner* — Keith O. Robinson
(74) *Attorney, Agent, or Firm* — Weatherly IP Solutions, LLC; Barbara Campbell

(57) ABSTRACT

A new cultivar of *Lomandra* named 'Olive Green' that is distinguishable by its numerous strap-like evergreen leaves which are formed into a dense plant habit which is arching, weeping and inwardly recurved and which bears sweetly fragrant inflorescences on short stems within the foliage canopy. In combination, these characteristics distinguish 'Olive Green' from all other varieties of *Lomandra* known to the inventor.

2 Drawing Sheets

Genus and species: *Lomandra confertifolia.*
Variety denomination: 'Olive Green'.

BACKGROUND

The present disclosure relates to a new and distinct cultivar of *Lomandra* plant, also known as mat-rush plant or spiny mat-rush, a perennial grass-like plant which is native to Australia and is grown for use as an ornamental landscape and container plant. The new variety will be referred to hereinafter by the cultivar name 'Olive Green'.

Commencing in 2008, the inventor established a breeding programme with the objective of developing novel varieties of *Lomandra* which are suitable for the commercial garden and landscape markets. In particular, the inventor wished to select varieties with robust performance in low maintenance landscape plantings.

In 2013, the inventor collected seed from a single plant of *Lomandra* 'Little Con' (unpatented) which seed had arisen from the open pollination of the inventor's collection of named *Lomandra* varieties and other unnamed seedlings which the inventor had raised previously. The collected seed was sown and the resultant seedlings were observed after two years' in-ground growth at the inventor's nursery in Longwarry, Victoria, Australia. One seedling, the present invention 'Olive Green' was selected by the inventor in 2013 primarily for its graceful weeping plant habit and robust performance in the landscape.

Asexual propagation of 'Olive Green' was first accomplished by the inventor in 2015 at the inventor's nursery in Longwarry, Victoria, Australia. The method of propagation used was division. Subsequent propagation has been achieved using the method of tissue culture in which small plantlets are established in vitro and divided. The inventor has confirmed that the characteristics of plants which have been propagated by traditional division and by laboratory micro propagation are fixed, uniform, and true to type.

SUMMARY

The following traits have been repeatedly observed and represent the distinguishing characteristics of 'Olive Green'. 'Olive Green' has not been tested under all possible conditions and phenotypic differences may be observed with variations in environmental, climatic, and cultural conditions, without however, any variance in genotype.

1. The foliage of 'Olive Green' consists of numerous strap-like leaves, which arise from a crown at or below soil level.
2. The plant habit of 'Olive Green' is arching, weeping and inwardly recurved.
3. 'Olive Green' is slow growing at first, requiring up to 18 months to fill out in a 1-gallon container.
4. 'Olive Green' may be propagated by division of its crown and by micro-propagation (tissue culture).
5. The foliage color of 'Olive Green' is green in color.
6. The inflorescences of 'Olive Green' consist of rigid panicles of small male flowers. The inflorescences are borne entirely within the foliage canopy.
7. The male flowers of 'Olive Green' are attractively bicolored brown (sepals) and yellow (petals) when the foliage is pried apart.
8. The inflorescence of 'Olive Green' is pleasant sweetly fragrant, reminiscent of citrus flowers.

DESCRIPTION OF THE DRAWINGS

The accompanying color drawings.

FIG. 1 depicts the arching and weeping habit of 'Olive Green' and the short inflorescences, which are borne entirely within the foliage canopy.

FIG. 2 depicts a close-up view of an inflorescence panicle, showing the bark brown sepals, the yellow petals and the straw-like bracts, which are borne at the base of each whorl.

Figure 1:
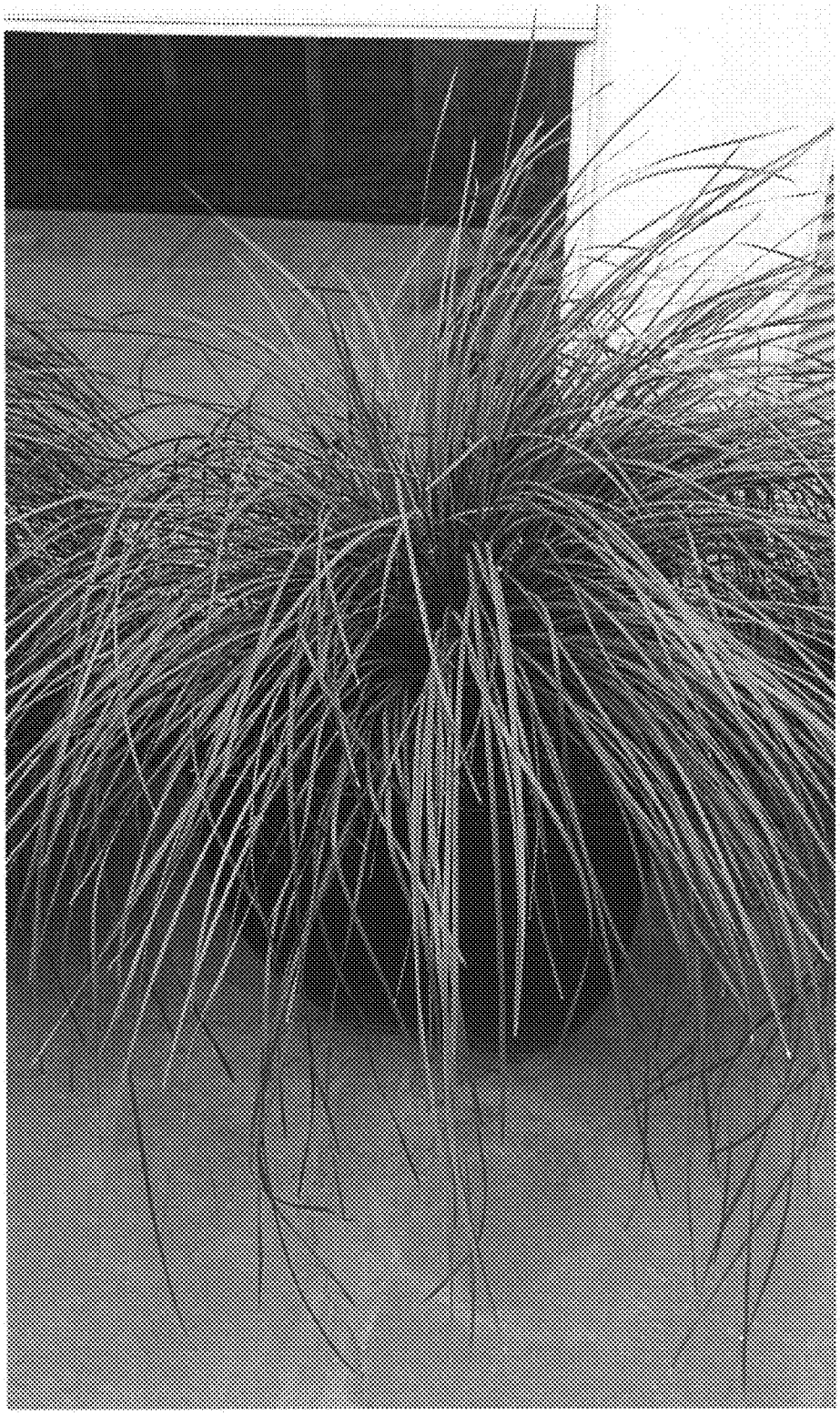
FIG. 1 and FIG. 2, illustrate the appearance of the new *Lomandra* cultivar 'Olive Green' showing the colors as true as it is reasonably possible to obtain in colored reproductions of this type.
Figure 2:
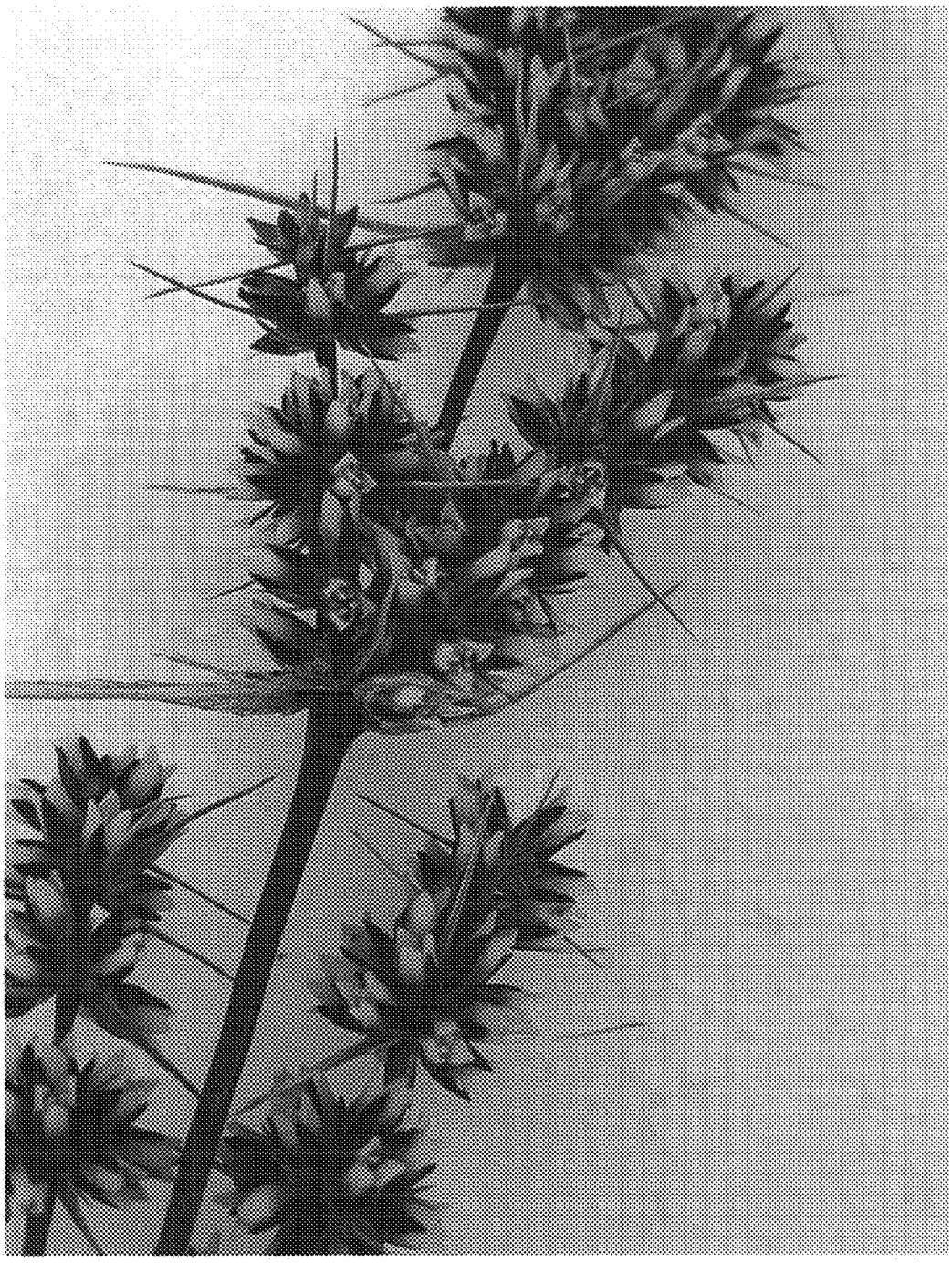

Photographs were taken in Spring 2018 in Oxnard, Calif. using an 18 months old plant (from a tissue culture plantlet) grown out of doors under a light shade structure.

DESCRIPTION OF THE NEW VARIETY

The following detailed descriptions set forth the distinctive characteristics of 'Olive Green'. Observations, measurements, values, and comparisons were collected in January 2020 in Santa Barbara, Calif. from a two-and-a-half year old plant which had been grown out of doors eventually in a 10 gallon container. The plant was grown from a tissue culture (in vitro) plantlet. The plant had been grown naturally, without any pinching or use of chemical growth regulator. Color determinations were made in accordance with The 2007 Royal Horticultural Society Colour Chart from London England, except where general color terms of ordinary dictionary significance are used.

Classification:

*Family*.—Asparagaceae.

*Genus*.—*Lomandra*.

*Species*.—*confertifolia*.

*Common name*.—Spiny-head mat-rush.

Parentage:

*Female parent*.—*Lomandra* 'Little Con'.

*Male parent*.—Unknown.

Plant:

*Propagation method*.—Division, tissue culture.

*Rooting system*.—Rhizomatous.

*Rhizomes*.—3 cm to 5 cm in length, 1 cm to 2 cm in diameter, scaly, giving rise to densely packed fine and fibrous rooting system.

*Rhizome and root color*.—RHS 197D.

*Vigor*.—Vigorous division at base forming an increasingly large crown with age.

*Time to develop roots*.—Approximately 6 weeks are required for a newly planted tissue culture plantlet to become established on its own roots.

*Crop time*.—Approximately 18 months required to produce a plant which fills out in a 1 gallon container. Larger and older plants may be produced for immediate impact in the landscape.

*Suggested container size*.—1 gallon container and larger if desired.

*Use*.—Ornamental for use as a landscape plant or container plant.

*Type*.—Perennial in USDA Zones 8 and above.

*Overall dimensions*.—35 cm in height, 90 cm in width (at widest level of arching foliage).

*Cultural requirements*.—Grow in full sun with moderate water and well-draining soil.

*Hardiness*.—USDA Zone 8.

*Growth habit*.—Dense crown from which arching and weeping foliage arises, becoming inwardly recurved.

*Blooming season*.—Spring until fall.

*Lastingness of blooms*.—Each inflorescence (panicle) has some flower for 14 days, individual flowers last for 5 to 7 days.

Leaves: 'Olive Green' bears evergreen weeping foliage in which the leaves arise directly from a surface crown. No stems or petioles are apparent.

*Shape*.—Simple, strap-like.

*Margins*.—Entire, parallel except for upper most 5 cm towards apex.

*Length*.—70 cm.

*Diameter*.—5 mm, tapering to 3 mm towards apex.

*Color*.—RHS 137C (both surfaces).

*Shape*.—Longitudinally concave.

*Surface texture* (*both surfaces*).—Smooth, glabrous, non-glaucous.

*Strength*.—Stiff, wiry.

*Aspect*.—Leaves initial vertical to approximately 20 cm in length, then bending, arching and eventually inwardly recurving.

*Venation*.—Parallel.

*Margin*.—Entire.

*Apex*.—2 or 3 toothed, each tooth ranging between 1 mm and 2.5 mm in length. Toothed section invariably necrotic, color 161D.

*Band* (*at interface between toothed apex and remainder of leaf blade*).—Narrow, 0.5 mm to 1.5 mm in width, color RHS 200A (both surfaces).

*Sheathing*.—Leaf is sheathed around culm for approximately 5 cm before becoming free. Width of sheath (when flattened) 8 mm to 13 mm. Color of sheath (adaxial surface): both RHS 183A and RHS 158C are present. Color of sheath (abaxial surface): RHS 158C.

*Base*.—Truncate.

Inflorescence:

*Type*.—Rigid panicle consisting of male flowers only; flowers borne in whorls along the rachis. Inflorescence is held entirely within the foliage mound.

*Dimensions*.—10 cm to 12 cm in overall length, 3 cm in overall diameter.

*Number of flowers per panicle*.—10 to 12 flowers per whorl, 30 to 35 whorls per panicle.

*Bloom period*.—Spring.

*Lastingness of some color in inflorescence*.—14 days.

*Fragrance of inflorescence*.—Sweet, as citrus blossom.

Peduncle:

*Length* (*to base of rachis*).—5 cm.

*Shape* (*section*).—Ellipsoidal.

*Width*.—4 mm.

*Depth*.—1.5 mm.

*Texture*.—Glaucous.

*Color*.—RHS 187A.

Pedicel: Absent on newest (uppermost) flowers towards apex.

*Length* (*lower, older flowers*).—Increasing to 5 cm.

*Diameter*.—0.5 mm.

*Shape*.—Round.

*Texture*.—Glaucous.

*Color*.—RHS 187A.

Bracts: Bracts present singly or in pair at base of each whorl.

*Shape*.—Narrowly lanceolate to needle-shaped apex.

*Dimensions*.—Up to 15 mm in length, 4 mm in width at truncate base.

*Texture, color*.—Dry, straw-like, RHS 158C.

Flowers: Dioecious, male only.

*Buds*.—Length: 2.5 mm. Diameter: 2.0 mm. Shape: Ovoid, apex subacute. Color: RHS N186C (unfused sepals such that petal color 13C is exposed).

*Sepals*.—Sepals: 3 in number, freely attached to base of calyx. Calyx base, small, rounded, approximately 1 mm in diameter, color RHS 199D. Sepal shape: Triangular, 3 mm in length, 1 mm in width at sepal base. Sepal surface, color (both surfaces): glossy, RHS N186C.

*Corolla*.—Very short tube, approximately 1 mm in length, petals soon free. Tube color: RHS 13C.

*Petals*.—Petals: 3 in number, rotate, protruding 1 mm beyond sepals. Shape: Triangular, 4 mm in length, 1 mm in width at petal base. Petal surface, color (both surfaces): Glossy, RHS 13C.

Reproductive organs: Dioecious, male flowers only. Stamens (up to 6 in number) evident under magnification, entirely inserted within short corolla tube. No other reproductive elements have been observed. Seed has not been observed.

Disease and pest resistance or susceptibility: None observed.

COMPARISON WITH PARENTAL LINES AND KNOWN VARIETY

'Olive Green' may be compared with the known female parent, *Lomandra* 'Little Con' by their respective plant habits. Whereas 'Little Con' grows with an upright plant habit, the plant habit of 'Olive Green' is arching and weeping. The identity of the male parent is unknown.

'Olive Green' may be compared with the *Lomandra* variety 'Emerald Grace' (unpatented). While the foliage of 'Olive Green' and 'Emerald Grace' are similarly mid-green in color, the leaves of 'Emerald Grace' are narrow and held upright, while the leaves of 'Olive Green' are broader and strap like, and are weeping.

I claim:

1. A new and distinct variety of *Lomandra* plant named 'Olive Green' as described and illustrated herein.

* * * * *